United States Patent
Lee

(10) Patent No.: US 10,471,000 B2
(45) Date of Patent: Nov. 12, 2019

(54) METHOD FOR MANUFACTURING ANTI-WRINKLE FUNTIONAL COSMETICS

(71) Applicant: Chung-Sig Lee, Gangneung-si (KR)

(72) Inventor: Chung-Sig Lee, Gangneung-si (KR)

( * ) Notice: Subject to any disclaimer, the term of this patent is extended or adjusted under 35 U.S.C. 154(b) by 195 days.

(21) Appl. No.: 15/370,869

(22) Filed: Dec. 6, 2016

(65) Prior Publication Data

US 2017/0246105 A1    Aug. 31, 2017

(30) Foreign Application Priority Data

Oct. 12, 2015  (KR) .................. 10-2015-0142209

(51) Int. Cl.
| | |
|---|---|
| *A61K 36/00* | (2006.01) |
| *A61K 36/23* | (2006.01) |
| *A61K 36/53* | (2006.01) |
| *A61K 36/64* | (2006.01) |
| *A61K 36/65* | (2006.01) |
| *A61K 36/70* | (2006.01) |
| *A61K 36/80* | (2006.01) |
| *A61K 36/73* | (2006.01) |
| *A61K 8/97* | (2017.01) |
| *A61K 8/19* | (2006.01) |
| *A61K 8/60* | (2006.01) |
| *A61K 8/92* | (2006.01) |
| *A61K 8/96* | (2006.01) |
| *A61K 8/98* | (2006.01) |
| *A61K 8/99* | (2017.01) |
| *A61Q 19/08* | (2006.01) |
| *C12P 1/04* | (2006.01) |
| *A61K 8/25* | (2006.01) |
| *A61K 8/9789* | (2017.01) |

(52) U.S. Cl.
CPC .................. *A61K 8/97* (2013.01); *A61K 8/19* (2013.01); *A61K 8/25* (2013.01); *A61K 8/606* (2013.01); *A61K 8/922* (2013.01); *A61K 8/927* (2013.01); *A61K 8/965* (2013.01); *A61K 8/9789* (2017.08); *A61K 8/987* (2013.01); *A61K 8/99* (2013.01); *A61Q 19/08* (2013.01); *C12P 1/04* (2013.01); *A61K 2800/591* (2013.01); *A61K 2800/5922* (2013.01); *A61K 2800/84* (2013.01); *A61K 2800/85* (2013.01)

(58) Field of Classification Search
None
See application file for complete search history.

(56) References Cited

U.S. PATENT DOCUMENTS

| | | | | |
|---|---|---|---|---|
| 2007/0248695 | A1* | 10/2007 | Kim ................ | A01G 2/00 424/728 |
| 2009/0104295 | A1* | 4/2009 | Kohno .............. | A61K 8/97 424/757 |
| 2009/0208470 | A1* | 8/2009 | Park ................. | A01N 63/04 424/93.51 |

FOREIGN PATENT DOCUMENTS

| | | |
|---|---|---|
| KR | 10-2014-0130596 | 11/2014 |
| KR | 10-2014-0145675 | 12/2014 |
| KR | 10-2015-0071080 | 6/2015 |
| KR | 10-1532003 | 6/2015 |

OTHER PUBLICATIONS

English translation of 10-2014-0130596.
English translation of 10-2014-0145675.
English translation of 10-1532003.
English translation of 10-2015-0071080.

* cited by examiner

*Primary Examiner* — Michael Barker
*Assistant Examiner* — Randall Winston
(74) *Attorney, Agent, or Firm* — Antonio Ha & U.S. Patent, LLC

(57) ABSTRACT

The present disclosure provides a method for preparing an anti-wrinkle functional cosmetic substance comprising cutting herbal materials comprising *Angelica gigas* root, *Rehmannia glutinosa* root, a paeonia *albiflora* root, *Mentha arvensis*, *Angelica dahurica* root, *Scrophularia buergeriana*, *Rheum undulatum* root/stalk/stem, *Sanguisorba officinalis* root, and *Cinnamomum cassia* bark into pieces, putting a mixture of the herbal material pieces, talc, a pearl powder, deep ocean water into an extractor, sterilizing the mixture, then fermenting the mixture by mixed lactobacillales strain, and then hot-water extracting the mixture into a solid, freeze-drying the extracted solid into a freeze-dried powder, and dissolving and high-speed mixing the freeze-dried powder, adenosine, and borax in a beeswax, a perilla oil, an *Olea europaea* (olive) fruit oil, and a *Helianthus annuus* (sunflower) seed oil heated and *Chamaecyparis obtusa* water heated.

7 Claims, 2 Drawing Sheets

METHOD FOR MANUFACTURING ANTI-WRINKLE FUNTIONAL COSMETICS

CROSS-REFERENCE TO RELATED APPLICATIONS

This patent application claims priority under 35 U.S.C. § 119 to Korean Patent Application No. 10-2015-0142209, filed on Oct. 12, 2015, in the Korean Intellectual Property Office, the disclosure of which is incorporated by reference herein in its entirety.

TECHNICAL FIELD

The present disclosure relates to a method for preparing cosmetics, more particularly to a method for preparing an anti-wrinkle functional cosmetic substance using herbal materials and natural minerals.

DISCUSSION OF RELATED ART

Cosmetic products, which enhance the appearance of skin, are increasingly in demand. Consumers are interested in mitigating or delaying the signs of chronologically or hormonally aged skin, as well as seeking alternatives to the costly and sometimes risky medical techniques currently available.

Active ingredients derived from plants and plant roots have commonly been employed in topical compositions for a myriad of medicinal, therapeutic and cosmetic purposes. Such actives can be obtained from various parts of a plant such as seeds, needles, leaves, roots, bark, cones, stems, rhizomes, callus cells, protoplasts, organs and organ systems, and meristems. Active ingredients are incorporated in such compositions in a variety of forms. Such forms include a pure or semi-pure component, a solid or liquid extract or derivative, or a solid plant matter. The functional use of these materials is novel and useful for the cosmetic industry.

Safe, effective and new components of compositions to treat, prevent, reduce, inhibit, and/or improve the dermatological signs of aging would be advantageous for the formulation of treatments and products for the skin. However, although these conventional cosmetic products include natural materials, inherent functions of a functional cosmetic are not much improved, and particularly the functional cosmetic might not be absorbed into a skin. If absorbed, it is apprehended that side effects such as an allergy may occur. As described herein, novel and beneficial methods and compositions, as well as their mode of action for personal care products for the skin, are provided by the present disclosure.

SUMMARY

According to an embodiment of the present disclosure, there is provided a method for preparing an anti-wrinkle functional cosmetic substance by mixing herbal materials with natural minerals and fermenting the mixture by mixed lactobacillales strain to increase inherent properties of herbal materials and natural minerals.

According to an embodiment of the present disclosure, there is provided a method for preparing an anti-wrinkle functional cosmetic substance by naturally fermenting raw materials into small molecules to well penetrate through skin and into amino acids and inorganic compositions similar as a skin moisturizing factor to decrease skin stimulus, increase skin moisturizing, and prevent pruritus.

According to an embodiment of the present disclosure, there is provided a method for preparing an anti-wrinkle functional cosmetic substance by extracting from herbal materials with deep ocean water to decrease oxidation and provide sufficient moisture and nutrition with skin so that skin vitality is regained to increase cosmetic function.

According to an embodiment of the present disclosure, there is provided a method for anti-wrinkle, applying a functional cosmetic substance prepared by the present disclosure to a skin of an object with an effective amount of the cosmetic substance.

According to an embodiment of the present disclosure, a method for preparing an anti-wrinkle functional cosmetic substance comprises cutting herbal materials comprising *Angelica gigas* root, *Rehmannia glutinosa* root, paeonia *albiflora* root, *Mentha arvensis*, *Angelica dahurica* root, *Scrophularia buergeriana*, *Rheum undulatum* root/stalk/stem, *Sanguisorba officinalis* root, and *Cinnamomum cassia* bark into pieces each measuring 0.5 cm to 1.0 cm in width and length, putting a mixture of the herbal material pieces, talc, a pearl powder, deep ocean water into an extractor, sterilizing the mixture at 100° C. to 110° C. for 50 minutes to 70 minutes, then fermenting the mixture by mixed lactobacillales strain at 37° C. to 43° C. for 69 hours to 75 hours, and then hot-water extracting the mixture into a solid, freeze-drying the extracted solid at −115° C. to −125° C. for 3 days to 5 days into a freeze-dried powder (ATM-1), and dissolving and high-speed mixing the freeze-dried powder (ATM-1), adenosine, and borax in a beeswax, a perilla oil, an *Olea europaea* (olive) fruit oil, and a *Helianthus annuus* (sunflower) seed oil heated at 62° C. to 68° C. and *Chamaecyparis obtusa* water heated at 34° C. to 40° C.

The functional cosmetic substance may comprise 0.15 weight % of an extract from the *Angelica gigas* root, 0.15 weight % of an extract from the *Rehmannia glutinosa* root, 0.15 weight % of an extract from the paeonia *albiflora* root, 0.15 weight % of an extract of the *Mentha arvensis*, 0.15 weight % of an extract from the *Angelica dahurica* root, 0.15 weight % of an extract from the *Scrophularia buergeriana*, 0.15 weight % of an extract from the *Rheum undulatum* root/stalk/stem, 0.3 weight % of an extract from the *Sanguisorba officinalis* root, 0.15 weight % of an extract of the *Cinnamomum cassia* bark, 0.04 weight % of the adenosine, 0.76 weight % of the borax, 0.15 weight % of the pearl powders, 1.45 weight % of the talc, 14.0 weight % of the beeswax, 25.0 weight % of the *Olea europaea* (olive) fruit oil, 20.0 weight % of the perilla oil, 10.0 weight % of the *Helianthus annuus* (sunflower) seed oil, and the *Chamaecyparis obtusa* water as a residue.

The functional cosmetic substance may be formed in any type ordinarily prepared in the art, for example, a milky type, a cosmetic a water type, a cream type, a lotion type, an emulsion type, an essence type, a pack type, a gel type, an ample type, or a mist type. Methods for preparing such types may be complied with known skills in the art.

The functional cosmetic substance may further comprise fat, an organic solvent, dissolvent, a concentrated agent, a gellant, a softner, an anti-oxidant, a suspending agent, a stabilizer, foaming agent, a flavoring agent, a surfactant, water, an ionic or a non-ionic emulsifying agent, a filling agent, a sequestering agent, a chelating agent, a vitamin, a blocking agent, a moisturizing agent, an essential oil, a dye, a pigment, a hydrophilic active agent, a lipophilic active agent, a lipid vesicle, or a supplemental agent such as certain different component ordinarily used in cosmetics, ordinarily used in field of Cosmetology or Dermatology.

According to an embodiment of the present disclosure, a method for preparing an anti-wrinkle functional cosmetic substance comprises cutting herbal materials comprising *Angelica gigas* root, *Rehmannia glutinosa* root, paeonia *albiflora* root, *Mentha arvensis*, *Angelica dahurica* root, *Scrophularia buergeriana*, *Rheum undulatum* root/stalk/stem, *Sanguisorba officinalis* root, and *Cinnamomum cassia* bark into pieces each measuring 0.5 cm to 1.0 cm in width and length, putting a mixture of the herbal material pieces, talc, a pearl powder, deep ocean water into an extractor, sterilizing the mixture at 100° C. to 110° C. for 50 minutes to 70 minutes, then fermenting the mixture by mixed lactobacillales strain at 37° C. to 43° C. for 69 hours to 75 hours, then sterilizing the mixture at 102° C. to 107° C. for 20 minutes, and then hot-water extracting the mixture into a solid, freeze-drying the extracted solid at −115° C. to −125° C. for 2 days to 4 days into a freeze-dried powder (ATM-1), and dissolving and high-speed mixing the freeze-dried powder (ATM-1), adenosine, and borax in *Chamaecyparis obtusa* water heated at 34° C. to 40° C.

The functional cosmetic substance may comprise 0.15 weight % of an extract from the *Angelica gigas* root, 0.15 weight % of an extract from the *Rehmannia glutinosa* root, 0.15 weight % of an extract from the paeonia *albiflora* root, 0.15 weight % of an extract of the *Mentha arvensis*, 0.15 weight % of an extract from the *Angelica dahurica* root, 0.15 weight % of an extract from the *Scrophularia buergeriana*, 0.15 weight % of an extract from the *Rheum undulatum* root/stalk/stem, 0.3 weight % of an extract from the *Sanguisorba officinalis* root, 0.15 weight % of an extract of the *Cinnamomum cassia* bark, 0.15 weight % of the pearl powders, 1.45 weight % of the talc, 0.76 weight % of the borax, 0.04 weight % of the adenosine, and the *Chamaecyparis obtusa* water as a residue.

The functional cosmetic substance may comprise 0.2 weight % of an extract from the *Angelica gigas* root, 0.2 weight % of an extract from the *Rehmannia glutinosa* root, 0.2 weight % of an extract from the paeonia *albiflora* root, 0.2 weight % of an extract of the *Mentha arvensis*, 0.2 weight % of an extract from the *Angelica dahurica* root, 0.2 weight % of an extract from the *Scrophularia buergeriana*, 0.2 weight % of an extract from the *Rheum undulatum* root/stalk/stem, 0.4 weight % of an extract from the *Sanguisorba officinalis* root, 0.2 weight % of an extract of the *Cinnamomum cassia* bark, 0.15 weight % of the pearl powders, 1.45 weight % of the talc, 0.04 weight % of the adenosine, 0.76 weight % of the borax, and the *Chamaecyparis obtusa* water as a residue.

The functional cosmetic substance may be formed in any type ordinarily prepared in the art, for example, a milky type, a cosmetic a water type, a cream type, a lotion type, an emulsion type, an essence type, a pack type, a gel type, an ample type, or a mist type. Methods for preparing such types may be complied with known skills in the art.

The functional cosmetic substance may further comprise fat, an organic solvent, dissolvent, a concentrated agent, a gellant, a softner, an anti-oxidant, a suspending agent, a stabilizer, foaming agent, a flavoring agent, a surfactant, water, an ionic or a non-ionic emulsifying agent, a filling agent, a sequestering agent, a chelating agent, a vitamin, a blocking agent, a moisturizing agent, an essential oil, a dye, a pigment, a hydrophilic active agent, a lipophilic active agent, a lipid vesicle, or a supplemental agent such as certain different component ordinarily used in cosmetics, ordinarily used in field of Cosmetology or Dermatology.

According to an embodiment of the present disclosure, there is provided an anti-aging method by applying an effective amount of functional cosmetic substance to a skin. The functional cosmetic substance comprises *Angelica gigas* root, *Rehmannia glutinosa* root, paeonia *albiflora* root, *Mentha arvensis*, *Angelica dahurica* root, *Scrophularia buergeriana*, *Rheum undulatum* root/stalk/stem, *Sanguisorba officinalis* root, and *Cinnamomum cassia* bark. The cosmetic substance optionally comprises a beeswax, a perilla oil, an *Olea europaea* (olive) fruit oil, and a *Helianthus annuus* (sunflower) seed oil.

The functional cosmetic substance may be prepared by a method comprising cutting herbal materials comprising the *Angelica gigas* root, the *Rehmannia glutinosa* root, the paeonia *albiflora* root, the *Mentha arvensis*, the *Angelica dahurica* root, the *Scrophularia buergeriana*, the *Rheum undulatum* root/stalk/stem, the *Sanguisorba officinalis* root, and the *Cinnamomum cassia* bark into pieces each measuring 0.5 cm to 1.0 cm in width and length, putting the herbal material pieces, the talc, the pearl powder, the deep ocean water into an extractor, sterilizing the mixture at 100° C. to 110° C. for 50 minutes to 70 minutes, then fermenting the mixture by mixed lactobacillales strain at 37° C. to 43° C. for 69 hours to 75 hours, and then hot-water extracting the mixture into a solid, freeze-drying the extracted solid at −115° C. to −125° C. for 3 days to 5 days into a freeze-dried powder (ATM-1) and dissolving and high-speed mixing the freeze-dried powder (ATM-1), the adenosine, and the borax in the beeswax, the perilla oil, the *Olea europaea* (olive) fruit oil, and the *Helianthus annuus* (sunflower) seed oil heated at 62° C. to 68° C. and *Chamaecyparis obtusa* water heated at 34° C. to 40° C.

The functional cosmetic substance may be prepared by a method comprising cutting herbal materials comprising the *Angelica gigas* root, the *Rehmannia glutinosa* root, the paeonia *albiflora* root, the *Mentha arvensis*, the *Angelica dahurica* root, the *Scrophularia buergeriana*, the *Rheum undulatum* root/stalk/stem, the *Sanguisorba officinalis* root, and the *Cinnamomum cassia* bark into pieces each measuring 0.5 cm to 1.0 cm in width and length, putting the herbal material pieces, talc, a pearl powder, deep ocean water into an extractor, sterilizing the mixture at 100° C. to 110° C. for 50 minutes to 70 minutes, then fermenting the mixture by mixed lactobacillales strain at 37° C. to 43° C. for 69 hours to 75 hours, then sterilizing the mixture at 102° C. to 107° C. for 20 minutes, and then hot-water extracting the mixture into a solid; freeze-drying the extracted solid at −115° C. to −125° C. for 2 days to 4 days into a freeze-dried powder (ATM-1), and dissolving and high-speed mixing the freeze-dried powder (ATM-1), the adenosine, and the borax in *Chamaecyparis obtusa* water heated at 34° C. to 40° C.

The functional cosmetic substance may comprise 0.15 weight % of an extract from the *Angelica gigas* root, 0.15 weight % of an extract from the *Rehmannia glutinosa* root, 0.15 weight % of an extract from the paeonia *albiflora* root, 0.15 weight % of an extract of the *Mentha arvensis*, 0.15 weight % of an extract from the *Angelica dahurica* root, 0.15 weight % of an extract from the *Scrophularia buergeriana*, 0.15 weight % of an extract from the *Rheum undulatum* root/stalk/stem, 0.3 weight % of an extract from the *Sanguisorba officinalis* root, 0.15 weight % of an extract of the *Cinnamomum cassia* bark, 0.04 weight % of the adenosine, 0.76 weight % of the borax, 0.15 weight % of the pearl powders, 1.45 weight % of the talc, 14.0 weight % of the beeswax, 25.0 weight % of the *Olea europaea* (olive) fruit oil, 20.0 weight % of the perilla oil, 10.0 weight % of the *Helianthus annuus* (sunflower) seed oil, and *Chamaecyparis obtusa* water as a residue.

The functional cosmetic substance may comprise 0.15 weight % of an extract from the *Angelica gigas* root, 0.15 weight % of an extract from the *Rehmannia glutinosa* root, 0.15 weight % of an extract from the paeonia *albiflora* root, 0.15 weight % of an extract of the *Mentha arvensis*, 0.15 weight % of an extract from the *Angelica dahurica* root, 0.15 weight % of an extract from the *Scrophularia buergeriana*, 0.15 weight % of an extract from the *Rheum undulatum* root/stalk/stem, 0.3 weight % of an extract from the *Sanguisorba officinalis* root, 0.15 weight % of an extract of the *Cinnamomum cassia* bark, 0.15 weight % of the pearl powders, 1.45 weight % of the talc, 0.76 weight % of the borax, 0.04 weight % of the adenosine, and *Chamaecyparis obtusa* water as a residue.

The functional cosmetic substance may comprise 0.2 weight % of an extract from the *Angelica gigas* root, 0.2 weight % of an extract from the *Rehmannia glutinosa* root, 0.2 weight % of an extract from the paeonia *albiflora* root, 0.2 weight %, of an extract of the *Mentha arvensis*, 0.2 weight % of an extract from the *Angelica dahurica* root, 0.2 weight % of an extract from the *Scrophularia buergeriana*, 0.2 weight % of an extract from the *Rheum undulatum* root/stalk/stem, 0.4 weight % of an extract from the *Sanguisorba officinalis* root, 0.2 weight % of an extract of the *Cinnamomum cassia* bark, 0.15 weight % of the pearl powders, 1.45 weight % of the talc, 0.04 weight % of the adenosine, 0.76 weight % of the borax, and *Chamaecyparis obtusa* water as a residue.

The functional cosmetic substance may be formed in any type ordinarily prepared in the art, for example, a milky type, a cosmetic a water type, a cream type, a lotion type, an emulsion type, an essence type, a pack type, a gel type, an ample type, or a mist type. Methods for preparing such types may be complied with known skills in the art.

The functional cosmetic substance may further comprise fat, an organic solvent, dissolvent, a concentrated agent, a gellant, a softner, an anti-oxidant, a suspending agent, a stabilizer, foaming agent, a flavoring agent, a surfactant, water, an ionic or a non-ionic emulsifying agent, a filling agent, a sequestering agent, a chelating agent, a vitamin, a blocking agent, a moisturizing agent, an essential oil, a dye, a pigment, a hydrophilic active agent, a lipophilic active agent, a lipid vesicle, or a supplemental agent such as certain different component ordinarily used in cosmetics, ordinarily used in field of Cosmetology or Dermatology.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF EXEMPLARY EMBODIMENTS

Figure 1:
FIG. 1 is a photo illustrating a state before applying a cream according to an embodiment 1 of the present disclosure.

Hereinafter, exemplary embodiments of the inventive concept will be described in detail with reference to the accompanying drawings. The inventive concept, however, may be modified in various different ways, and should not be construed as limited to the embodiments set forth herein. The same reference denotations may be used to refer to the same or similar elements throughout the specification and the drawings. As used herein, the singular forms "a," "an," and "the" are intended to include the plural forms as well, unless the context clearly indicates otherwise. The words or terms used herein should not be construed to be limited as having their ordinary or dictionary meanings but rather be construed based on the meanings and concepts corresponding to technical aspects of the present disclosure according to the principle that the inventor can define terms and words to describe his/her disclosure.

Thus, it should be appreciated that the embodiments described and shown herein are exemplary embodiments of the present disclosure and do not represent all of the technical features of the present disclosure so that there may be, as of the time of filing, other various equivalents and modifications thereto.

Embodiment 1

According to an embodiment 1 of the present disclosure, herbal materials and natural minerals are used as raw materials, and deep ocean water is used when extracting the raw materials into a solid so that property of antioxidation is increased. The solid is fermented by mixed lactobacillales strain to enable a polymer to be converted into a small molecule so that skin stimulus is minimized the cosmetic substance is easily absorbed into a skin to increase moisturizing and makeup effect. A method for preparing such anti-wrinkle functional cosmetic substance comprises four steps, and hereinafter each step is described in detail.

A first step is to cut herbal materials into pieces. The herbal materials comprise *Angelica gigas* root, *Rehmannia glutinosa* root, a paeonia *albiflora* root, *Mentha arvensis*, *Angelica dahurica* root, *Scrophularia buergeriana*, *Rheum undulatum* root/stalk/stem, *Sanguisorba officinalis* root, and *Cinnamomum cassia* bark. Each piece is measured 0.5 cm to 1.0 cm in width and length to be easily extracted.

The *Angelica gigas* root is used as a skin conditioning agent supplementing and activating blood, recovering a damaged skin, curing abscess, and relieving a pain.

The pehmannia root is used as a skin conditioning agent stopping a variety of bleeding, reducing a fever, enabling to well urinate, and removing extravasated blood. When the pehmannia root is used with the *Angelica giga* root, it is complementary to each other.

The paeonia *albiflora* root is used a skin gelatinizing agent recovering a damaged skin and a skin with a stagnant extravasated blood to supplement blood, and having effects on relieve from a pain and hemostatic reaction so that blood is well circulated to prevent an erratic menstruation.

The *Mentha arvensis* has a menthol as a main component, having effects on activating a rash, producing cooling, medical-used in an embrocation, a pain reliever, a stimulant, a stomachic, and an anthelmintic, and used as a cooler or flavoring in a toothpaste, a jam, a candy, a cosmetic, a cigarette, etc.

The *Angelica dahurica* root is used as a skin conditioning agent, scenting with drying and heating so that rheumatism is cured, and itchiness and a pain are relieved.

The *Rheum undulatum* root/stalk/stem relieves a fever by throwing an anger off to cool a fever, reduces an infection, and has effects on a long-lasting extravasated blood and a new extravasated blood.

The *Sanguisorba officinalis* root recovers a skin damage, has an effect on an eczema, and relieves a fever to heal a wound.

The *Cinnamomum cassia* bark is used as a skin moisturizing agent and a skin elasticity agent, warms a skin to relieve a pain and heal a wound, and is well known as a medical herb warming an inner body.

Although it is effective that each extract from the herbal materials is independently used, if mixed herbal materials are used, it is more effective because their disadvantage are supplemented.

As above described, the herbal materials are cut into pieces each measuring 0.5 cm to 1.0 cm in width and length. Such size of the herbal materials enables the pieces to be easily extracted with hot-water in a following second step.

The second step puts the cut herbal materials into deep ocean water, ferments the mixture by mixed lactobacillales strain, and hot-water extracts the fermented mixture into a solid. The deep ocean water provides sufficient moisture and nutrition with skin so that skin vitality is regained, and a face line is tense to be a clear baby face.

A talc and a pearl powder are used as a natural mineral. The talc is excellent skin protective and absorptive to enable the skin to be smoothed, and is widely used to remove moisture such as sweat. The pearl powder includes various types of minerals and bioactive substances so that a pigment colored on the skin is lighter to enable skin tone to be brightened, and is good for the skin as well as an exfoliation of dead skin cells.

The hot-water extraction is a method using a hot water to separate a soluble material. The hot-water extraction refers to an ordinary extraction process widely used on extraction of the soluble material.

As per an exemplary embodiment of the present disclosure, the fermentation process and the hot water extraction are executed at 37° C. to 43° C., or at 40° C., for 72 hours until the hot water extract is solubilized A third step freeze-dries the extracted solid. The freeze-drying is a method freezing the extracted solid at −115° C. to −125° C. for 3 days to 5 days to dry the extracted solid by evaporation or sublimation.

According to an exemplary embodiment of the present disclosure, in order easily to produce a powder as a freeze-dried powder (ATM-1), the freeze-drying is executed at −115° C. to −125° C. for 3 days to 5 days, or at −120° C. for 4 days.

A fourth step dissolves and mixes the freeze-dried powder (ATM-1), adenosine, and borax in a beeswax, a perilla oil, an *Olea europaea* (olive) fruit oil, and a *Helianthus annuus* (sunflower) seed oil heated at 62° C. to 68° C. and *Chamaecyparis obtusa* water heated at 34° C. to 40° C.

The adenosine has an effect on anti-wrinkles as described in website of Korea ministry of food and drug safety (http://www.mfds.go.kr).

The beeswax, the perilla oil, the *Olea europaea* (olive) fruit oil, and the *Helianthus annuus* (sunflower) seed oil are mixed in order to produce a functional cosmetic product as a type of a cream such as a hand cream, The beeswax is a mass of an oil boiling a residue after a honey is squeezed from a bee's hive, boosting vitality, quickly healing wounds, and controlling detoxication and a pain. The perilla oil has effects on preventing skin aging, recovering a damaged skin, and anti-oxidation reaction. The *Helianthus annuus* (sunflower) seed oil has effects on immunity improvement, smoothing a chapped skin by a semi-drying oil, blood circulation, and artery hardening. The *Olea europaea* (olive) fruit oil has many antioxidative components and is well absorbed through a cell membrane so that a chemical substance is easily transferred into a cell.

The above-described substances are fatty acids. According to an exemplary embodiment of the present disclosure, in order to easily mix the substances with the freeze-dried powder, the substances are heated at a predetermined temperature. For example, the beeswax is heated at 62° C. to 68° C., or at 65° C., and then the perilla oil, the *Olea europaea* (olive) fruit oil, and the *Helianthus annuus* (sunflower) seed oil are put in the heated beeswax, and the mixture should be maintained.

According to an exemplary embodiment of the present disclosure, the freeze-dried powder, the adenosine, and the borax are dissolved in the *Chamaecyparis obtusa* water heated at 34° C. to 40° C. or at 37° C.

According to an exemplary embodiment of the present disclosure, a functional cosmetic substance prepared by the above-described method is of a cream type such as a hand cream type.

The functional cosmetic substance comprises 0.15 weight % of an extract from the *Angelica gigas* root, 0.15 weight % of an extract from the *Rehmannia glutinosa* root, 0.15 weight % of an extract from the *paeonia albiflora* root, 0.15 weight % of an extract of the *Mentha arvensis*, 0.15 weight % of an extract from the *Angelica dahurica* root, 0.15 weight % of an extract from the *Scrophularia buergeriana*, 0.15 weight % of an extract from the *Rheum undulatum* root/stalk/stem, 0.3 weight % of an extract from the *Sanguisorba officinalis* root, 0.15 weight % of an extract of the *Cinnamomum cassia* bark, 0.04 weight % of the adenosine, 0.76 weight % of the borax, 0.15 weight % of the pearl powders, 1.45 weight % of the talc, 14.0 weight % of the beeswax, 25.0 weight of the *Olea europaea* (olive) fruit oil, 20.0 weight % of the perilla oil, 10.0 weight % of the *Helianthus annuus* (sunflower) seed oil, and the *Chamaecyparis obtusa* water as a residue.

Figure 2:
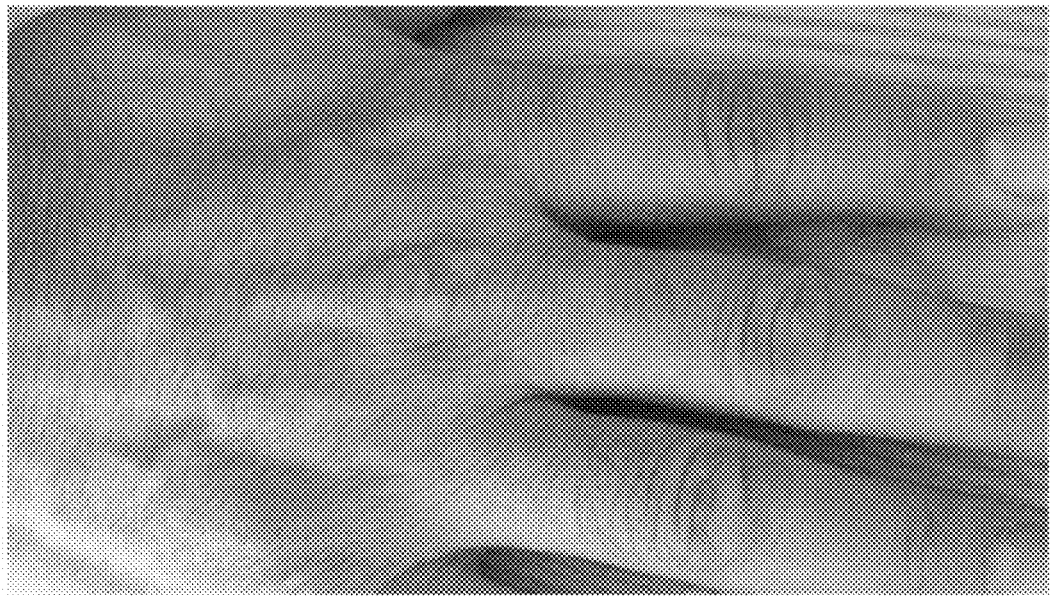
FIG. 2 is a photo illustrating a state after one month from applying a cream according to the embodiment 1 of the present disclosure.
Figure 3:
FIG. 3 is a photo illustrating a state before applying a cream according to the embodiment 1 of the present disclosure.
Figure 4:
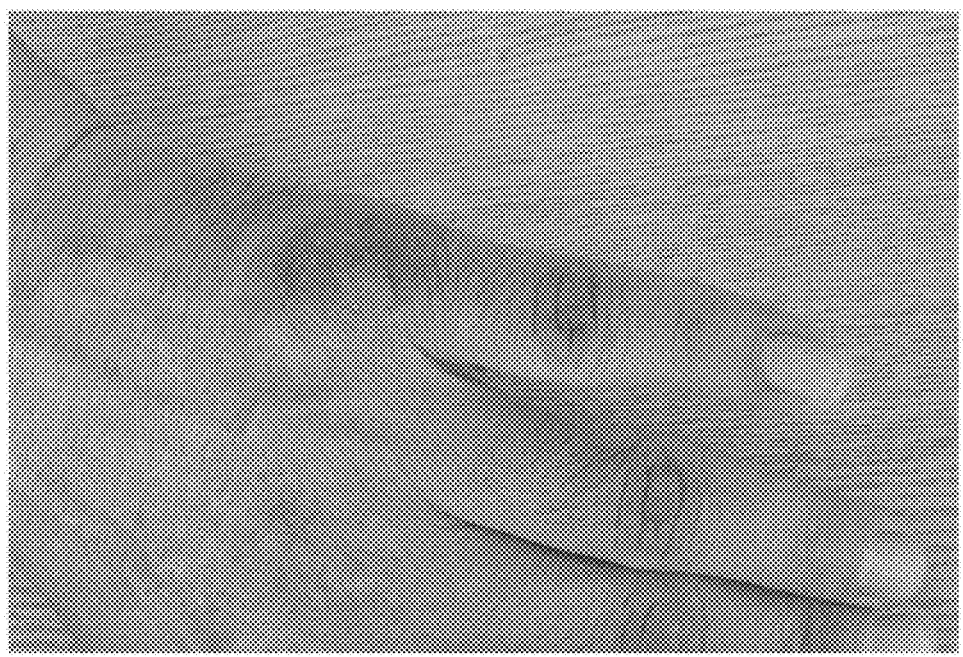
FIG. 4 is a photo illustrating a state after one month from applying a cream according to the embodiment 1 of the present disclosure.

The functional cosmetic product as a type of a cream according to the above-described present disclosure was regularly applied to an object for one month. FIG. 1 is a photo illustrating a state before applying the cream. FIG. 2 is a photo illustrating a state after one month from applying the cream. FIG. 3 is a photo illustrating a state before applying the cream. FIG. 4 is a photo illustrating a state after one month from applying the cream. As illustrated in FIGS. 1 to 4, a portion shown as a red color before use had largely disappeared, and a dead skin cell on a back of the object's hand was removed to made a clear impression. Furthermore, in contrast to a chapped hand before use due to itchiness, etc., after use, anti-wrinkle effect was improved. In other words, results after using the cosmetic product showed effects on reducing itchiness, removing an epithelial dead skin cell, moisturizing, and reducing dryness.

Embodiment 2

An anti-wrinkle functional cosmetic substance according to an embodiment 2 of the present disclosure, in contrast to a cream-type such as a hand cream of the embodiment 1, is used as a spray-type or a liquid-type such as a skin lotion.

The embodiments 1 and 2 use same herbal materials and natural minerals. The same compositions are briefly described, and the difference is described in detail.

As per the embodiment 2, a method for a functional cosmetic substance comprises cutting herbal materials, hot-water extracting the cut materials into a solid, and freeze-drying the extracted solid which are same as ones of the embodiment 1. Therefore, detailed descriptions for these processes are excluded herein.

However, as per the embodiment 2, a fourth step mixes the freeze-dried powder, the adenosine, and borax with *Chamaecyparis obtusa* water heated at 34° C. to 40° C. in order that the cosmetic substance is used as a spray-type or liquid-type, while the embodiment 1 mixes the freeze-dried powder, the adenosine, and borax with the beeswax with oils such as the perilla oil, the *Olea europaea* (olive) fruit oil, and the *Helianthus annuus* (sunflower) seed oil.

The functional cosmetic substance according to the method of the above-described embodiment 2 is used as a liquid-type or a spray-type.

According the embodiment 2 of the present disclosure, the cosmetic substance comprises 0.15 weight % of an extract from the *Angelica gigas* root, 0.15 weight % of an extract from the *Rehmannia glutinosa* root, 0.15 weight % of an extract from the paeonia *albiflora* root, 0.15 weight % of an extract of the *Mentha arvensis,* 0.15 weight % of an extract from the *Angelica dahurica* root, 0.15 weight % of an extract from the *Scrophularia buergeriana,* 0.15 weigh % of an extract from the *Rheum undulatum* root/stalk/stem, 0.3 weight % of an extract from the *Sanguisorba officinalis* root, 0.15 weight % of an extract of the *Cinnamomum cassia* bark, 0.15 weight % of the pearl powders, 1.45 weight % of the talc, 0.76 weight % of the borax, 0.04 weight % of the adenosine, and the *Chamaecyparis obtusa* water as a residue.

Therefore, the present disclosure can prepare a functional cosmetic preventing a natural cosmetic to be changed by interaction among extracts from a herb, natural minerals, and deep ocean water, enabling nutritional component to be converted to small molecules by fermentation and aging by a mixed lactobacillales strain, decreasing skin stimulus, being easily absorbed, reducing allergic reaction and itchiness, decreasing widths of the epithelium and dermis, and helps a blast cell to be developed.

Embodiment 3

A method for preparing an anti-wrinkle functional cosmetic substance according to an embodiment 3 of the present disclosure comprises a same method as the embodiment 2 except their compositions are different. Thus, the compositions are described herein.

A functional cosmetic substance according to the embodiment 3 comprises 0.2 weight % of an extract from the *Angelica gigas* root, 0.2 weight % of an extract from the *Rehmannia glutinosa* root, 0.2 weight % of an extract from the paeonia *albiflora* root, 0.2 weight % of an extract of the *Mentha arvensis,* 0.2 weight % of an extract from the *Angelica dahurica* root, 0.2 weight % of an extract from the *Scrophularia buergeriana,* 0.2 weight % of an extract from the *Rheum undulatum* root/stalk/stem, 0.4 weight % of an extract from the *Sanguisorba officinalis* root, 0.2 weight % of an extract of the *Cinnamomum cassia* bark, 0.15 weight/o of the pearl powders, 1.45 weight % of the talc, 0.04 weight % of the adenosine, 0.76 weight % of the borax, and the *Chamaecyparis obtusa* water as a residue.

According to the embodiments of the present disclosure, a method for preparing an anti-wrinkle functional cosmetic substance, since the functional cosmetic substance uses herbal materials and natural minerals as raw materials, may minimize side effects.

Further, since deep ocean water is used to draw extracts from the herbal materials, the functional cosmetic substance, despite a long time use, may be well preserved without deteriorating anti-oxidation capability.

Also, the herbal materials and natural minerals are fermented by the mixed lactobacillales strain so that compositions of the functional cosmetic substance are formed in small molecules, thus leading to a minimized skin stimulus and easier absorption of the cosmetic substance through the skin. Therefore, a better makeup effect may be achieved.

Further, the natural fermentation of herbal materials and natural minerals may reduce skin allergic reactions and itchiness.

Further, such low-molecular compositions include amino acids or inorganic elements similar to a natural moisturizing composition, providing for a minimized skin stimulus and better moisturizing effect.

The cosmetic substance includes adenosine, increasing an anti-wrinkle function.

While the inventive concept has been shown and described with reference to exemplary embodiments thereof, it will be apparent to those of ordinary skill in the art that various changes in form and detail may be made thereto without departing from the spirit and scope of the inventive concept as defined by the following claims.

What is claimed is:

1. A method for preparing an anti-wrinkle functional cosmetic substance, the method comprising:
   cutting herbal materials comprising *Angelica gigas* root, *Rehmannia glutinosa* root, a paeonia *albiflora* root, *Mentha arvensis, Angelica dahurica* root, *Scrophularia buergeriana, Rheum undulatum* root/stalk/stem, *Sanguisorba officinalis* root, and *Cinnamomum cassia* bark into herbal material pieces, each of the herbal material pieces measuring 0.5 cm to 1.0 cm in width and length;
   putting a mixture of the herbal material pieces, talc, a pearl powder, deep ocean water into an extractor, sterilizing the mixture at 100° C. to 110° C. for 50 minutes to 70 minutes, then fermenting the mixture using mixed lactobacillales strain at 37° C. to 43° C. for 69 hours to 75 hours, and then hot-water extracting the fermented mixture into a solid;
   freeze-drying the extracted solid at −115° C. to −125° C. for 3 days to 5 days into a freeze-dried powder (ATM-1); and
   dissolving the freeze-dried powder (ATM-1), adenosine, and borax in a beeswax, a perilla oil, an *Olea europaea* (olive) fruit oil, and a *Helianthus annuus* (sunflower) seed oil heated at 62° C. to 68° C. or in *Chamaecyparis obtusa* water heated at 34° C. to 40° C. and high-speed mixing the freeze-dried powder (ATM-1), adenosine, and borax together.

2. The method of claim 1, wherein the functional cosmetic substance comprises 0.15 weight % of *Angelica gigas* root extract, 0.15 weight % of the *Rehmannia glutinosa* root extract, 0.15 weight % of paeonia *albiflora* root extract, 0.15 weight % of *Mentha arvensis* extract, 0.15 weight % of *Angelica dahurica* root extract, 0.15 weight % of *scrophularia buergeriana* extract, 0.15 weight % of *Rheum undulatum* root/stalk/stem extract, 0.3 weight % of *Sanguisorba officinalis* root extract, 0.15 weight % of *Cinnamomum cassia* bark extract, 0.04 weight % of the adenosine, 0.76 weight % of the borax, 0.15 weight % of the pearl powders, 1.45 weight % of the talc, 14.0 weight % of the beeswax, 25.0 weight % of the *Olea europaea* (olive) fruit oil, 20.0 weight % of the perilla oil, 10.0 weight % of the *Helianthus annuus* (sunflower) seed oil, and the *Chamaecyparis obtusa* water as a residue.

3. The method of claim 1, wherein the functional cosmetic substance is of a milky type, a water type, a cream type, a lotion type, an emulsion type, an essence type, a pack type, a gel type, an ample type, or a mist type.

4. A method for preparing an anti-wrinkle functional cosmetic substance, the method comprising:
cutting herbal materials comprising *Angelica gigas* root, *Rehmannia glutinosa* root, paeonia *albiflora* root, *Mentha arvensis*, *Angelica dahurica* root, *Scrophularia buergeriana*, *Rheum undulatum* root/stalk/stem, *Sanguisorba officinalis* root, and *Cinnamomum cassia* bark into herbal material pieces, each of the herbal material pieces measuring 0.5 cm to 1.0 cm in width and length;
putting a mixture of the herbal material pieces, talc, a pearl powder, deep ocean water into an extractor, sterilizing the mixture at 100° C. to 110° C. for 50 minutes to 70 minutes, then fermenting the mixture by mixed lactobacillales strain at 37° C. to 43° C. for 69 hours to 75 hours, then sterilizing the mixture at 102° C. to 107° C. for 20 minutes, and then hot-water extracting the sterilized mixture into a solid;
freeze-drying the extracted solid at −115° C. to −125° C. for 2 days to 4 days into a freeze-dried powder (ATM-1); and
dissolving the freeze-dried powder (ATM-1), adenosine, and borax in *Chamaecyparis obtusa* water heated at 34° C. to 40° C. and high-speed mixing the freeze-dried powder (ATM-1), adenosine, and borax together.

5. The method of claim 4, wherein the functional cosmetic substance comprises 0.15 weight % of *Angelica gigas* root extract, 0.15 weight % of *Rehmannia glutinosa* root extract, 0.15 weight % of paeonia *albiflora* root extract, 0.15 weight % of *Mentha arvensis* extract, 0.15 weight % of *Angelica dahurica* root extract, 0.15 weight % of *scrophularia buergeriana* extract, 0.15 weight % of *Rheum undulatum* root/stalk/stem extract, 0.3 weight % of *Sanguisorba officinalis* root extract, 0.15 weight % of *Cinnamomum cassia* bark extract, 0.15 weight % of the pearl powders, 1.45 weight % of the talc, 0.76 weight % of the borax, 0.04 weight % of the adenosine, and the *Chamaecyparis obtusa* water as a residue.

6. The method of claim 4, wherein the functional cosmetic comprises 0.2 weight % of *Angelica gigas* root extract, 0.2 weight % of *Rehmannia glutinosa* root extract, 0.2 weight % of paeonia *albiflora* root extract, 0.2 weight % of *Mentha arvensis* extract, 0.2 weight % of *Angelica dahurica* root extract, 0.2 weight % of *Scrophularia buergeriana* extract, 0.2 weight % of *Rheum undulatum* root/stalk/stem extract, 0.4 weight % of *Sanguisorba officinalis* root extract, 0.2 weight % of *Cinnamomum cassia* bark extract, 0.15 weight % of the pearl powders, 1.45 weight % of the talc, 0.04 weight % of the adenosine, 0.76 weight % of the borax, and the *Chamaecyparis obtusa* water as a residue.

7. The method of claim 4, wherein the functional cosmetic substance is of a milky type, a water type, a cream type, a lotion type, an emulsion type, an essence type, a pack type, a gel type, an ample type, or a mist type.

* * * * *